United States Patent
Kono et al.

(10) Patent No.: US 6,943,138 B2
(45) Date of Patent: Sep. 13, 2005

(54) OIL CLEARING SHEET FOR MAKEUP

(75) Inventors: Yasuhiro Kono, Kanagawa (JP);
Kazunori Kondoh, Tokyo (JP)

(73) Assignee: 3M Innovative Properties Company, St. Paul, MN (US)

( * ) Notice: Subject to any disclaimer, the term of this patent is extended or adjusted under 35 U.S.C. 154(b) by 571 days.

(21) Appl. No.: 10/276,086

(22) PCT Filed: Jun. 4, 2001

(86) PCT No.: PCT/US01/17945
§ 371 (c)(1),
(2), (4) Date: Nov. 15, 2002

(87) PCT Pub. No.: WO01/97669
PCT Pub. Date: Dec. 27, 2001

(65) Prior Publication Data
US 2003/0211954 A1 Nov. 13, 2003

(30) Foreign Application Priority Data
Jun. 16, 2000 (JP) .................. 2000-185941

(51) Int. Cl.$^7$ ............................... A47K 10/16
(52) U.S. Cl. ........................................ 510/136
(58) Field of Search ............................... 510/136

(56) References Cited

FOREIGN PATENT DOCUMENTS

| EP | 04189639 | | 7/1992 |
|----|----------|---|--------|
| EP | 0997142 | | 5/2000 |
| EP | 1 035 793 B1 | | 7/2003 |
| GB | 2 061 709 | * | 5/1981 |
| JP | 56-8606 | | 1/1981 |
| JP | 04-045591 | | 2/1992 |
| JP | 5-18392 | | 3/1993 |
| JP | 63-19664 | | 11/1994 |
| WO | WO 99/29220 | | 6/1999 |

* cited by examiner

Primary Examiner—Yogendra N. Gupta
Assistant Examiner—John M Petruncio
(74) Attorney, Agent, or Firm—Gary L. Griswold; Robert W. Sprague; William J. Bond (57) ABSTRACT

To provide an oil clearing sheet for makeup, which is superior in capacity to absorb oil and can confirm the wiping state of sebum easily and clearly, and which can afford sufficient wiping feeling and satisfactory feeling to users. An oil clearing sheet for makeup, comprising a porous stretched film of a plastic material, characterized in that the porous stretched film comprises at least two porous stretched films, which are the same or different, and adjacent films differ in brightness.

6 Claims, 1 Drawing Sheet

FIG. 1

OIL CLEARING SHEET FOR MAKEUP

FIELD OF THE INVENTION

The present invention relates to an oil clearing sheet for makeup and, more particularly, to an oil clearing sheet for makeup used for wiping oil (sebum) of the skin oozed out on the face.

BRIEF DESCRIPTION OF THE INVENTION

It has hitherto been well known that various oil clearing papers are used for wiping sebum oozed out on the portion such as face, particularly nose, cheek, forehead, and middle of forehead, thereby to maintain the face clean and to improve applicability and spreadability of a cosmetic composition. The reason is as follows. That is, when making up in the state where sebum is oozed out on the face, a cosmetic composition is not easily applied on the skin and, therefore, the spreadability of the cosmetic composition becomes poor, thereby making it impossible to sufficiently exert the makeup effect. The oil clearing paper also has an effect to prevent makeup from coming off and to prevent "shining face", previously, by absorption of sebum oozed out from the skin with a lapsed time after making up, using the oil clearing paper.

A conventional oil clearing paper is generally produced by using papers and plastic materials (e.g. thermoplastic polymer) as a raw material. For example, an oil clearing paper made of paper is produced by using vegetable fibers having a capacity to absorb oil, such as hemp, synthetic pulp, and kenaf. However, the oil clearing paper made of paper has such a drawback as to give high stimulation to the skin because of hardness and surface roughness of the fiber material to be used. To improve such stimulation to the skin, strong roll press is conducted and the surface of the paper is coated with inorganic powders such as calcium carbonate powders, together with a sizing agent, on production of the oil clearing paper. However, the former case has such a drawback that fibers pressed by roll press changes to a raised state with a lapsed time, thereby stimulating the skin again, while the latter case has such a drawback that lowering of a capacity to absorb sebum can not be avoided because the surface of the paper is coated with the sizing agent.

In addition, the oil clearing paper made of paper has a comparatively small capacity to absorb oil and the appearance of the paper hardly changes when absorbed sebum. Therefore, it is difficult to confirm the degree of absorption of sebum, that is to say, wiping state of sebum.

To solve various drawbacks and problems described above, the oil clearing paper has widely been improved. For example, Japanese Examined Utility Model Publication (KOKOKU) No. 4-45591 teaches that porous spherical beads are adhered on the surface of an oil clearing paper so as to solve the problems caused, when roll press is conducted and the surface of the paper is coated with inorganic powders such as calcium carbonate powders on production of the oil clearing paper, and to increase the capacity to absorb sebum. Japanese Unexamined Patent Publication (KOKAI) No. 6-319664 discloses a high-density oil clearing paper produced by mixing (A) a pulp material containing vegetable fibers as a main component with (B) an inorganic filler to prepare a paper material, followed by paper-making so that the weight (g/cm$^2$) of the paper is 0.7 or more.

The oil clearing paper made of paper disclosed in these publications has limitation in capacity to absorb sebum because its main material is made of paper and, particularly significantly, it is difficult to confirm the degree of absorption of sebum, that is, wiping state easily and accurately in use because a change in permeability is hardly recognized in the paper itself. Difficulty in confirming the wiping state of sebum means that users of the oil clearing paper do not satisfy with removal of sebum from the face. It is a very significant evaluation point for users how much sebum was removed from the users' face by using the oil clearing paper, and satisfaction on makeup can vary largely whereby.

An oil clearing paper for makeup developed by paying attention to facilitate the wiping state of sebum as described above has been publicly known, heretofore. For example, Japanese Examined Patent Publication (KOKOKU) No. 56-8606 discloses a cosmetic oil clearing paper produced by mixing hemp fibers with 10 to 70% by weight of polyolefin resin fibers, followed by paper-making so that the weight of the paper is within a range from 12 to 50 (g/cm$^2$). Japanese Unexamined Utility Model Publication (KOKAI) No. 5-18392 discloses an oil clearing paper comprising an oil clearing paper body and an inorganic or organic powder material such as clay particles, silica fine-particles, and powders of fibers, the surface of the oil clearing paper being formed smoothly. These oil clearing papers can exert some effect with respect to clarification of the oil clearing paper due to oil absorption and confirmation of the oil absorbing effect whereby, however, the absorption capacity as a most significant factor for the oil clearing paper is lowered as a result of a deleterious influence and it is difficult to attain complete clarification in the oil clearing paper after oil absorption.

As described above, an oil clearing paper produced by using a plastic material in place of papers is also publicly known. For example, Japanese Unexamined Patent Publication (KOKAI) No. 9-335451 discloses an oil clearing sheet made of a porous film produced by using a plastic material as a main raw material. Not only this oil clearing sheet has higher absorption capacity than that of the oil clearing paper made of paper, but also it is superior in confirmation of the wiping state to the oil clearing paper made of paper. The reason is as follows. That is, the porous plastic film exhibits low transmittance before oil absorption because of irregular reflection of light, but the transmittance increase remarkably because micro-pores of the film are filled with oils, thereby to facilitate confirmation of the wiping state. However, in case where light transmission in the film is not complete because of incomplete filling of micro-pores of the film with fats and oils, it becomes difficult to confirm the wiping state as a matter of course. To increase the capacity to absorb oil, the thickness of the film may be increased. In that case, it is necessary to fill the micro-pores of the film with a large amount of fats and oils and it becomes difficult to completely attain a predetermined level of transmittance. It also becomes necessary to take a long time for clearing oil, thereby to prevent a quick treatment as an essential object of oil clearing.

Furthermore, confirmation of the wiping state may be accelerated by coloring the oil clearing paper. However, the color, which facilitate confirmation of the wiping state, is limited to deep color such deep blue and deep green, while the color such as white, yellow and pastel, which has a tendency to be generally loved by users, maintains difficulty in confirming the wiping state.

DETAILED DESCRIPTION OF THE PREFERRED EMBODIMENT

It is, therefore, an object of the present invention to solve the above-described problems of a conventional oil clearing paper for makeup and to provide an improved oil clearing sheet, which is superior in capacity to absorb oil and can confirm the wiping state easily and clearly because it becomes transparent when absorbed oil, and which can afford sufficient wiping feeling and satisfactory feeling to users.

According to the present invention, there is provided an oil clearing sheet for makeup comprising a porous stretched film of a plastic material, characterized in that the porous stretched film comprises at least two porous stretched films, which are the same or different, and adjacent films differ in brightness.

The oil clearing sheet according to the present invention is formed of a porous stretched film of a plastic material, and the porous stretched film is composed of a laminate of at least two porous stretched films, which are the same or different, and adjacent films differ in brightness.

In the oil clearing sheet of the present invention, by satisfying the above-described constituent features, one film layer is clarified when it absorbed sebum and sweat after wiping them so that it reflects the color of another film layer, which is adjacent to the transparent film layer, thereby making it possible to clearly indicate the wiping state. Such an effect is derived from the fact that adjacent films differ in brightness. This difference in brightness exerts a large influence on the visibility of the film and has relation to ease of confirming the wiping state.

In the oil clearing sheet of the present invention, the brightness of the porous stretched film is advantageously represented by a value of L* of a CIEL*a*b* color system. The value of L* represents dark and light (black and white) and the color becomes whiter as L* approaches 100, whereas, the color becomes blacker as L* approaches 0. Assumed that a difference obtained by subtracting L* of the film after oil absorption from L* of the film before oil absorption is δL* when measured by the reflection process, δL* becomes smaller as L* approaches 100, thereby making it difficult to confirm the wiping state.

In the oil clearing sheet of the present invention, the film at the side to be made contact with the skin (porous stretched film as an uppermost layer) has preferably a value of L* which is different from that of the inside film (underlying layer) which is adjacent to the film. As described previously, users tend to prefer a color having a high value of L*, that is, pale color, however, such a color has a small value of δL* and it is difficult to confirm the wiping state. Therefore, it is more preferred in the oil clearing sheet of the present invention that a film having a large value of L* is disposed as the porous stretched film which is the uppermost layer to be made contact with the skin, and then the other porous stretched film having a value of L* smaller than that of the uppermost layer on formation of its multi-layer. A difference between the value of L* of the porous stretched film as the uppermost layer and the value of L* of the underlying film can vary depending on the desired effect, but is preferably at least 0.8.

The oil clearing sheet according to the present invention is characterized in that a plastic material is used without using papers as a main raw material like a conventional oil clearing paper and, moreover, the material is in the form of a two- or multi-layer porous stretched film. The plastic material used for formation of the porous stretched film may be formed only of the same material or formed of different materials according to the desired effect. Portion of the porous stretched film used in the present invention may be replaced by a non-porous stretched or non-stretched film, if necessary. For example, in case of a three-layer or five-layer structure oil clearing sheet, a core film may be composed of a plastic film free from micro-pores.

The porous stretched film of the present invention is not limited, but preferably has the following layer constitution:
(1) film A/film B,
(2) film A/film B/film A, or
(3) film A/film B/film C/film B/film A. It is particularly preferred to employ a constitution which is symmetrical in the thickness direction, such as layer constitutions (2) and (3), because the same operation and effect can be obtained in back and front surfaces of the oil clearing sheet and the wiping efficiency is very good.

In the embodiment of the above-described layer constitution, the film A is a porous stretched film as the uppermost layer and this film A and the film B as the ground can preferably have different values of L* while satisfying the relation about size. In such a layer constitution, the film A, film B and film C are preferably made of the same material, but may be made of different materials, if necessary. Furthermore, the respective films may be made of films, which have the same color but differ in tone, e.g. pale color and deep color, as far as they can satisfy the features of different values of L*. For example, the porous stretched film may be made of films having different colors, such as white/blue and yellow/red. Furthermore, in case of the layer constitution (3), the film C as the core material may be made of a film free from micro-pore, if necessary.

The porous stretched film having a multi-layer structure according to the present invention can be produced according to various procedures using a plastic material as a starting substance, but is preferably produced by adding a filler to a crystalline thermoplastic resin having high transparency to give a main raw material, molding the main raw material to form a plastic film, and stretching this film thereby to afford micro-pores. This procedure will be described below.

The porous stretched plastic film thus obtained is superior in capacity to absorb sebum on the skin surface because a proportion of space occupied in the volume of the sheet is larger than that of a conventional oil clearing paper. Accordingly, the capacity to absorb oil per unit area is remarkably large. Since this plastic film has such a structure as to contain lots of micro-pores uniformly, it is opaque because of diffusion of light before wiping sebum on the skin surface. However, since diffusion of light is prevented or relieved by filling the respective pores with sebum after oil absorption, the transparency as an intrinsic property of the film appears again and the visible effect of the color of the ground film is accelerated, thereby making it possible to confirm the wiping state of sebum easily and clearly.

In the production of the porous stretched film of the present invention, preferred examples of the crystalline thermoplastic resin having high transparency used as a main raw material include, but are not limited to, polyolefins such as high-density polyethylene, polypropylene, modified polypropylene, and polybutylene; polyesters; polyamides; poly-4-methylpentene, and ethylene-propylene block copolymer. Among them, polypropylene and modified polypropylene are particularly preferred because of melt strength on film forming.

Preferred examples of the filler used in combination with the above thermoplastic resin so as to afford micro-pores include, but are not limited to, organic materials such as mineral oil, glycerin, petroleum jelly, low-molecular polyethylene, polyethylene oxide, polypropylene oxide, polytetramethylene oxide, and soft carbowax; or inorganic materials such as calcium carbonate.

Various fillers can be used in the raw material used on production of the film. Suitable amount of the filler is within a range from 20 to 60% by mass (% by weight), and more preferably from 25 to 40% by mass, based on the raw material. When the amount of the filler is smaller than 20% by mass based on the raw material, since the porosity of the film obtained after stretching is lowered, the capacity to absorb oil is lowered. On the other hand, when the amount is larger than 60% by mass, it becomes difficult to form a film and only a brittle film can be obtained.

In the production of the porous stretched plastic film, other additives may also be added optionally, in addition to the thermoplastic resin and filler as the main raw material. For the purpose of facilitating crystallization of the main raw material, an organic nucleating agent may be added. Suitable organic nucleating agent includes, for example, organic acids such as carboxylic acid, sulfonic acid, and phosphonic acid; or organic alcohol. Other suitable additives include, for example, inorganic or organic pigments or dyes, perfumes, surfactants, lubricants, and antistatic agents. Among these additives, inorganic or organic pigments or dyes are capable of improving visibility through coloring of the film, thereby enhancing the reliability of the operation of confirming the wiping state. Therefore, it is preferred that most preferred one is selected according to the desired effect and then mixed in a suitable amount.

To obtain a multi-layer plastic film containing a filler, various procedures can be used. In the present invention, requisite number of mixtures obtained by melting and mixing the above main raw materials and optional additives may be preferably molded at the same time. This melting/mixing process and the subsequent process can be conducted according to a conventional procedure. Suitable melting/mixing process includes, for example, kneading using kneader. Suitable molding process includes, for example, co-extrusion process, preferably inflation process, T-die process, and cast process. For example, according to the inflation process, a film can be made by melting and mixing the above main raw materials and blowing the mixture through a circular die. For example, according to the cast process, a film can be made by melting and mixing the above main raw materials and extruding the mixture on a chill roll (cooling roll) through a die. According to one modification of this cast process, the melt mixture can be removed by washing with a suitable solvent after extruding on the chill roll. At this stage, stretching of the film, which is usually carried out in the subsequent process, may be carried out at the same time.

Next, stretching of the plastic film after film forming is conducted to afford micro-pores. The stretching can also be conducted monoaxially or biaxially according to a conventional method in the same manner as in case of film forming. In case of biaxial stretching, stretching in the longitudinal direction can be conducted by changing a circumferential speed of a driving roll whereas, stretching in the width direction can be conducted by mechanically stretching the film in the lateral direction while gripping right and left ends of the film with chucks.

Conditions of film stretching are not specifically limited, but the film is preferably stretched so that the porosity and thickness of the film after stretching are within the following preferred range. In that case, a stretching ratio of the film can vary widely, but is preferably within a range from 1.5 to 3.0. When the stretching ratio is smaller than 1.5, porosity enough to absorb oil can not be obtained. On the other hand, when the stretching ratio is larger than 3.0, since the pore diameter becomes too large, the capacity to absorb oil becomes larger and touch to hands becomes poor before changing the color.

The pore diameter of pores formed by stretching the film is preferably within a range from 0.2 to 5 $\mu$m. When the pore diameter is smaller than 0.2 $\mu$m, the absorption rate of sebum is lowered, thereby making it difficult to fill micro-pores with sebum and to obtain a predetermined level of transparency. On the other hand, when the pore diameter is larger than 5 $\mu$m, irregular reflection before oil absorption is prevented and the transmittance before oil absorption is increased, thereby making it difficult to obtain a difference in transmittance between the film before oil absorption and that after oil absorption.

A proportion of the above pores occupied in the porous stretched plastic film according to the present invention, that is, porosity is preferably within a range from 5 to 50%. When the porosity obtained by stretching is smaller than 5%, the capacity to absorb oil is too lowered. On the other hand, when the porosity is larger than 50%, micro-pores can not be completely filled with sebum and the transmittance on oil absorption can not be increased sufficiently.

The thickness of the porous stretched plastic film according to the present invention can vary widely depending on the desired effect. The thickness of such a porous film is preferably within a range from 1 to 100 $\mu$m in view of the thickness of each film constituting the porous film. When the thickness of each film is smaller than 1 $\mu$m, not only production of the porous film becomes difficult, but also micro-pores are easily filled with sebum, thereby causing lowering of the transmittance of plural films. On the other hand, when the thickness of each film is larger than 100 $\mu$m, micro-pores are not easily filled with sebum, thereby making it difficult to confirm the wiping state.

The whole thickness of the porous stretched plastic film is preferably within a range from 2 to 200 $\mu$m, and more preferably from 5 to 200 $\mu$m. When the whole thickness of the film is smaller than 2 $\mu$m, the capacity to absorb oil is lowered and the film is adhered to the portion of the face where oil clearing is not required, resulting in difficult handling. The upper limit of the whole thickness of the film is not specifically limited, but is not too large because too large upper limit causes too large capacity to absorb oil and increase in production cost. The thickness of a conventional single-layer structure oil clearing sheet is limited to 100 $\mu$m or less. On the other hand, in the porous stretched plastic film of the present invention, the thickness of one oil clearing sheet is further increased to 100 $\mu$m or more by employing a multi-layer structure, thereby making it possible to realize more enhanced capacity to absorb oil without making it difficult to confirm the wiping state.

The oil clearing sheet of the present invention can exert such a remarkable effect as to have an excellent capacity to absorb sebum and to cause remarkable clarification as an index for confirmation of the wiping state of sebum. However, such an oil clearing sheet made of a plastic material is likely to fail in absorption of water such as sweat as compared with the oil clearing sheet made of paper. The present inventors have studied intensively to solve such drawbacks and found that low capacity to absorb sweat is exclusively caused by hydrophobicity of the surface of the plastic sheet, so that sweat on the face and sebum dissolved into sweat can be easily absorbed by imparting hydrophilicity to the surface of the sheet. In the oil clearing sheet of the present invention, it is preferred that a hydrophilic liquid absorbing substance is partially distributed on at least oil absorbing surface of the porous stretched film.

The distribution state of the hydrophilic liquid absorbing substance in a hydrophilic oil clearing sheet is usually the state where fine-particles are dispersed on the surface of the porous stretched film nearly uniformly. Various methods can be employed to apply the liquid absorbing substance, and the liquid absorbing substance may also be contained in the film. In case where the oil clearing sheet is designed so as to use only one surface, the liquid absorbing substance may be distributed only on one surface of the porous stretched film, or may be distributed on both faces.

The application of the hydrophilic liquid absorbing substance can be made by using various methods. For example, the liquid absorbing substance can be advantageously applied by coating on the surface of the porous stretched film after producing the porous stretched film. In case of this method, a desired hydrophilic oil clearing sheet can be produced by dissolving a liquid absorbing substance in a suitable solvent, coating one or both surfaces of the porous stretched film with the resulting coating solution using a suitable procedure, drying the coating solution and removing the solvent.

The hydrophilic liquid absorbing substance, which can be advantageously used in the production of the hydrophilic oil clearing sheet, is not specifically limited as far as it can exert the expected operation and effect, but is preferably a surfactant. The reason is as follows. In case of the present invention, when liquid (droplets) such as sweat on the face is wiped, it is necessary that the liquid absorbing substance is incorporated into the droplets thereby to lower the surface tension of the droplets. To do so, presence of a substance capable of exhibiting remarkable surface activity at low concentration, that is, a surfactant is effective. It has previously described that various additives can be added to raw materials in the production of a plastic film and a surfactant is included as one example thereof, however, the surfactant in this case is not added for the purpose of imparting the hydrophilicity, but for the purpose of supplementing good dispersion of additives on kneading of the raw materials.

The surfactant suited for use as the hydrophilic liquid absorbing substance includes, but is not limited to:

anionic surfactant such as alkyl sulfate ester, alkyl benzenesulfonate salt, and polyoxyethylene alkyl phosphate ester;

nonionic surfactant such as polyoxyethylene alkyl ether, sorbitan fatty acid ester, and polyoxyethylene sorbitan fatty acid ester;

cationic surfactant such as alkylamine salt, and quaternary ammonium salt; and hydrophilic polymer such as polyvinyl alcohol, polyethylene glycol, and polypropylene glycol. Among them, sorbitan fatty acid ester represented by sorbitan monolaurate can be used particularly advantageously because it is superior in impartation of hydrophilicity and is also superior in safety to the skin.

In case where the coating solution is prepared from the above-described hydrophilic liquid absorbing substance, suitable solvent includes, but is not limited to, isopropyl alcohol, ethanol, water, methyl ethyl ketone, toluene, ethyl acetate, and heptane. Among these solvents, isopropyl alcohol can be used particularly advantageously because it has comparatively high solubility to the liquid absorbing substance and high volatility.

The concentration of the hydrophilic liquid absorbing substance in the coating solution can vary widely depending on the kind and degree of surface activity of the liquid absorbing substance to be used, and the desired effect, but is preferably an enough amount so that the capacity to absorb liquid of the porous stretched film after imparting the hydrophilicity is within a range from 0.00003 to 0.005 $cm^3$ per unit area in case where the amount is represented with respect to the water absorption amount of the film. When the capacity to absorb liquid deviates from the above range, it is impossible to obtain satisfactory capacity to absorb sweat in the resulting cosmetic oil clearing sheet. Preferred range of such capacity to absorb liquid is a standard which can be applied to the resulting whole cosmetic oil clearing sheet.

The surface tension of an aqueous solution of the liquid absorbing substance distributed on the surface of the porous stretched film is preferably within a range from 15.0 to 36.0 dyn/cm. When the surface tension of the surface of the porous stretched film deviates from the above range, satisfactory capacity to absorb sweat can not be obtained in the resulting oil clearing sheet and, in case where the degree of sweat absorption and oil clearing is evaluated by a change in color of the oil clearing sheet, this film can not be used effectively.

In case where the coating solution is coated on the porous stretched film, a coating operation can be conducted according to a conventional procedure. Preferred coating method includes, for example, gravure coating, flexo-coating, screen coating, dip coating, and spray coating. The coating weight of the coating solution on the surface of the porous stretched film can vary widely depending on the kind and degree of surface activity of the liquid absorbing substance to be used, and the desired effect, but is sufficiently from about 0.1 to 3 $g/m^2$.

In the production of the oil clearing sheet according to the present invention, a method of mixing the liquid absorbing substance in the film during the production process of the porous stretched film can be employed in place of the coating method described above. In the production of the porous stretched film, a desired hydrophilic oil clearing sheet can be produced by mixing the liquid absorbing substance at any time when a thermoplastic resin, a filler and an organic solvent as raw materials of the film are molten and mixed. Also in case of such a method, the liquid absorbing substance described with respect to application of the liquid absorbing substance due to coating can be used in the same manner. The amount thereof is preferably an amount enough to secure the above-described capacity to absorb liquid. In case of such a method, diethanolamide laurate can be used particularly advantageously in view of the heat resistance and hydrophilicity of the substance itself, among various usable liquid absorbing substances.

EXAMPLES

Subsequently, the present invention will be described with reference to the examples. In the following examples, "parts" means "parts by weight", unless otherwise stated.

Example 1

Preparation of Melt Mixture A

The following raw materials were molten and mixed in the amount described below to prepare a melt mixture A.

| | |
|---|---|
| Polypropylene resin (available from Union Carbide under the tradename of "5D45") | 65.0 parts |
| Mineral oil (available from Amco Oil & Chemical Co. under the tradename of "White Mineral Oil #31") | 35.0 parts |

Preparation of Melt Mixture B

The following raw materials were molten and mixed in the amount described below to prepare a melt mixture B.

| | |
|---|---|
| Polypropylene resin (available from Union Carbide under the tradename of "5D45") | 63.6 parts |
| Mineral oil (available from Amco Oil & Chemical Co. under the tradename of "White Mineral Oil #31") | 35.0 parts |
| Blue pigment (available from Clariant Co. under the trade name of "Renafin Blue APY5014A") | 1.4 parts |

Production of Oil Clearing Sheet

The resulting melt mixtures A and B were cast on a cooling roll through a co-extrusion die so that a film derived from the melt mixture B is sandwiched between films derived from the melt mixture A, thereby to form a film. Then, the resulting laminate (film A/film B) was biaxially stretched (1.8 times in a longitudinal direction, 1.8 times in a width direction) to obtain a porous stretched plastic film wherein a pale blue film B is sandwiched between white films A. The feature of this porous film is as follows.

| | |
|---|---|
| Thickness of film (whole thickness) | 105 μm |
| Thickness of film A | 35 μm |
| Thickness of film B | 35 μm |
| Porosity | 30% |

The resulting porous film was cut into rectangular pieces having a length of 9 cm and a width of 6 cm to make test films, and then a monitor test by twenty panelists was carried out. As a result, it has been found that this test film exhibits good feeling to the skin and excellent effect of removing oil and can judge the wiping state of oil easily and clearly by a remarkable change in color (remarkable development of color of a ground film B due to clarification of a film A) when used as a cosmetic oil clearing sheet. This film was not broken during the evaluation test.

After laying five test films (having a length of 9 cm and a width of 6 cm) one upon another, the chromaticity (value of L*) was measured according to the reflection process. A colorimeter used herein is manufactured by Nippon Denshoku Kogyo Co. under the trade name of "SZ-EΣ80". To measure the chromaticity (value of L*) after oil absorption, five films were laid one upon another and then dipped in a commercially available mineral oil. After allowing to stand for 1 minute, oil remained on the film surface was wiped by a paper towel and the chromaticity was measured again according to the reflection process.

As a result, the following results were obtained.

| | |
|---|---|
| Value of L* before oil absorption | 90.66 |
| Value of L* after oil absorption | 71.33 |

It became apparent that δL*, that is, (value of L* before oil absorption)—(value of L* after oil absorption) is 19.33 and it is possible to confirm the wiping state very satisfactorily. Further, the L* values (before oil absorption) of the films A and B were 98.33 and 68.1, respectively, and thus the difference in the L* value between these films was 30.23. The measurement results of this example are summarized in Table 1 below, together with those of the other examples.

Example 2

The procedure described in Example 1 was repeated, except that the film A and film B were respectively prepared from the following melt mixtures in this example.

| | |
|---|---|
| Composition of Melt Mixture A | |
| Polypropylene resin (aforecited) | 63.6 parts |
| Mineral oil (aforecited) | 35.0 parts |
| Blue pigment (aforecited) | 1.4 parts |
| Composition of Melt Mixture B | |
| Polypropylene resin (aforecited) | 62.25 parts |
| Mineral oil (aforecited) | 35.00 parts |
| Blue pigment (aforecited) | 2.75 parts |

There was obtained a porous stretched plastic film wherein a blue film B is sandwiched between pale blue films A. The feature of this porous film is as follows.

| | |
|---|---|
| Thickness of film (whole thickness) | 105 μm |
| Thickness of film A | 35 μm |
| Thickness of film B | 35 μm |
| Porosity | 32% |

Further, the L* values (before oil absorption) of the films A and B were 68.1 and 61.04, respectively, and thus the difference in the L* value between these films was 7.06.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 3

The procedure described in Example 1 was repeated, except that the film A and film B were respectively prepared from the following melt mixtures in this example.

| Composition of Melt Mixture A | |
|---|---|
| Polypropylene resin (aforecited) | 5.0 parts |
| Mineral oil (aforecited) | 35.0 parts |
| Composition of Melt Mixture B | |
| Polypropylene resin (aforecited) | 2.25 parts |
| Mineral oil (aforecited) | 35.00 parts |
| Blue pigment (aforecited) | 2.75 parts |

There was obtained a porous stretched plastic film wherein a blue film B is sandwiched between white films A. The feature of this porous film is as follows.

| Thickness of film (whole thickness) | 05 $\mu$m |
|---|---|
| Thickness of film A | 35 $\mu$m |
| Thickness of film B | 35 $\mu$m |
| Porosity | 32% |

Further, the L* values (before oil absorption) of the films A and B were 98.33 and 61.04, respectively, and thus the difference in the L* value between these films was 37.29.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 4

The procedure described in Example 1 was repeated, except that the film A and film B were respectively prepared from the following melt mixtures in this example.

| Composition of Melt Mixture A | |
|---|---|
| Polypropylene resin (aforecited) | 5.0 parts |
| Mineral oil (aforecited) | 35.0 parts |
| Composition of Melt mixture B | |
| Polypropylene resin (aforecited) | 2.25 parts |
| Mineral oil (aforecited) | 35.00 parts |
| Blue pigment (aforecited) | 2.75 parts |

There was obtained a porous stretched plastic film wherein a blue film B is sandwiched between white films A. The feature of this porous film is as follows.

| Thickness of film (whole thickness) | 39 $\mu$m |
|---|---|
| Thickness of film A | 13 $\mu$m |
| Thickness of film B | 13 $\mu$m |
| Porosity | 39% |

Further, the L* values (before oil absorption) of the films A and B were 98.33 and 61.04, respectively, and thus the difference in the L* value between these films was 37.29.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 5

The procedure described in Example 1 was repeated, except that the film A and film B were respectively prepared from the following melt mixtures in this example.

| Composition of Melt Mixture A: | |
|---|---|
| Polypropylene resin (aforecited) | 5.0 parts |
| Mineral oil (aforecited) | 35.0 parts |
| Composition of Melt Mixture B: | |
| Polypropylene resin (aforecited) | 2.50 parts |
| Mineral oil (aforecited) | 35.00 parts |
| Green pigment | 3.25 parts |
| (available from Clariant Co. under the tradename of "Renafin Green AEY003A") | |

There was obtained a porous stretched plastic film wherein a pale green film B is sandwiched between white films A. The feature of this porous film is as follows.

| Thickness of film (whole thickness) | 105 $\mu$m |
|---|---|
| Thickness of film A | 35 $\mu$m |
| Thickness of film B | 35 $\mu$m |
| Porosity | 30% |

Further, the L* values (before oil absorption) of the films A and B were 98.33 and 85.99, respectively, and thus the difference in the L* value between these films was 12.34.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 6

The procedure described in Example 1 was repeated, except that the film A and film B were respectively prepared from the following melt mixtures in this example.

| Composition of Melt Mixture A: | |
|---|---|
| Polypropylene resin (aforecited) | 62.50 parts |
| Mineral oil (aforecited) | 35.00 parts |
| Green pigment (aforecited) | 3.25 parts |
| Composition of Melt Mixture B: | |
| Polypropylene resin (aforecited) | 58.5 parts |
| Mineral oil (aforecited) | 35.0 parts |
| Green pigment (aforecited) | 6.5 parts |

There was obtained a porous stretched plastic film wherein a green film B is sandwiched between pale green films A. The feature of this porous film is as follows.

| | |
|---|---|
| Thickness of film (whole thickness) | 105 μm |
| Thickness of film A | 35 μm |
| Thickness of film B | 35 μm |
| Porosity | 31% |

Further, the L* values (before oil absorption) of the films A and B were 85.99 and 68.69, respectively, and thus the difference in the L* value between these films was 17.33.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 7

The procedure described in Example 1 was repeated, except that the film A and film B were respectively prepared from the following melt mixtures in this example.

| | |
|---|---|
| Composition of melt mixture A: | |
| Polypropylene resin (aforecited) | 65.00 parts |
| Mineral oil (aforecited) | 35.00 parts |
| Composition of melt mixture B: | |
| Polypropylene resin (aforecited) | 58.5 parts |
| Mineral oil (aforecited) | 35.0 parts |
| Green pigment (aforecited) | 6.5 parts |

There was obtained a porous stretched plastic film wherein a green film B is sandwiched between white films A. The feature of this porous film is as follows.

| | |
|---|---|
| Thickness of film (whole thickness) | 105 μm |
| Thickness of film A | 35 μm |
| Thickness of film B | 35 μm |
| Porosity | 31% |

Further, the L* values (before oil absorption) of the films A and B were 98.33 and 68.69, respectively, and thus the difference in the L* value between these films was 29.64.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 8

The procedure described in Example 1 was repeated, except that the film A and film B were respectively prepared from the following melt mixtures in this example.

| | |
|---|---|
| Composition of Melt Mixture A | |
| Polypropylene resin (aforecited) | 65.0 parts |
| Mineral oil (aforecited) | 35.0 parts |
| Composition of Melt Mixture B | |
| Polypropylene resin (aforecited) | 58.5 parts |
| Mineral oil (aforecited) | 35.0 parts |
| Green pigment (aforecited) | 6.5 parts |

There was obtained a porous stretched plastic film wherein a green film B is sandwiched between white films A. The feature of this porous film is as follows.

| | |
|---|---|
| Thickness of film (whole thickness) | 39 μm |
| Thickness of film A | 13 μm |
| Thickness of film B | 13 μm |
| Porosity | 38% |

Further, the L* values (before oil absorption) of the films A and B were 98.33 and 68.69, respectively, and thus the difference in the L* value between these films was 29.64.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 9

The procedure described in Example 1 was repeated, except that the film A and film B were respectively prepared from the following melt mixtures in this example.

| | |
|---|---|
| Composition of melt mixture A: | |
| Polypropylene resin (aforecited) | 65.0 parts |
| Mineral oil (aforecited) | 35.0 parts |
| Composition of Melt Mixture B: | |
| Polypropylene resin (aforecited) | 64.6 parts |
| Mineral oil (aforecited) | 35.0 parts |
| Red pigment (available from Clariant Co. under the tradename of "Renafin Red APY3034A") | 0.4 parts |

There was obtained a porous stretched plastic film wherein a pale red (pink) film B is sandwiched between white films A. The feature of this porous film is as follows.

| Thickness of film (whole thickness) | 105 μm |
|---|---|
| Thickness of film A | 35 μm |
| Thickness of film B | 35 μm |
| Porosity | 33% |

Further, the L* values (before oil absorption) of the films A and B were 98.33 and 80.24, respectively, and thus the difference in the L* value between these films was 18.09.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 10

The procedure described in Example 1 was repeated, except that the film A and film B were respectively prepared from the following melt mixtures in this example.

| Composition of Melt Mixture A: | |
|---|---|
| Polypropylene resin (aforecited) | 64.6 parts |
| Mineral oil (aforecited) | 35.0 parts |
| Red pigment (aforecited) | 0.4 parts |
| Composition of Melt Mixture B: | |
| Polypropylene resin (aforecited) | 64.3 parts |
| Mineral oil (aforecited) | 35.0 parts |
| Red pigment (aforecited) | 0.7 parts |

There was obtained a porous stretched plastic film wherein a red film B is sandwiched between pink films A. The feature of this porous film is as follows.

| Thickness of film (whole thickness) | 105 μm |
|---|---|
| Thickness of film A | 35 μm |
| Thickness of film B | 35 μm |
| Porosity | 38% |

Further, the L* values (before oil absorption) of the films A and B were 80.24 and 61.29, respectively, and thus the difference in the L* value between these films was 18.95.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 11

The procedure described in Example 1 was repeated, except that the film A and film B were respectively prepared from the following melt mixtures in this example.

| Composition of Melt Mixture A | |
|---|---|
| Polypropylene resin (aforecited) | 65.0 parts |
| Mineral oil (aforecited) | 35.0 parts |
| Composition of Melt Mixture B | |
| Polypropylene resin (aforecited) | 64.3 parts |
| Mineral oil (aforecited) | 35.0 parts |
| Red pigment (aforecited) | 0.7 parts |

There was obtained a porous stretched plastic film wherein a red film B is sandwiched between white films A. The feature of this porous film is as follows.

| Thickness of film (whole thickness) | 105 μm |
|---|---|
| Thickness of film A | 35 μm |
| Thickness of film B | 35 μm |
| Porosity | 33% |

Further, the L* values (before oil absorption) of the films A and B were 98.33 and 61.29, respectively, and thus the difference in the L* value between these films was 37.04.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 12

The procedure described in Example 1 was repeated, except that the film A and film B were respectively prepared from the following melt mixtures in this example.

| Composition of Melt Mixture A: | |
|---|---|
| Polypropylene resin (aforecited) | 65.0 parts |
| Mineral oil (aforecited) | 35.0 parts |
| Composition of melt mixture B: | |
| Polypropylene resin (aforecited) | 63.75 parts |
| Mineral oil (aforecited) | 35.00 parts |
| Yellow pigment (available from Clariant Co. under the tradename of "Renafin Yellow APY1016A") | 1.25 parts |

There was obtained a porous stretched plastic film wherein a pale yellow film B is sandwiched between white films A. The feature of this porous film is as follows.

| Thickness of film (whole thickness) | 105 μm |
|---|---|
| Thickness of film A | 35 μm |
| Thickness of film B | 35 μm |
| Porosity | 32% |

Further, the L* values (before oil absorption) of the films A and B were 98.33 and 95.27, respectively, and thus the difference in the L* value between these films was 3.06.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 13

The procedure described in Example 1 was repeated, except that the film A and film B were respectively prepared from the following melt mixtures in this example.

| Composition of Melt Mixture A | |
| --- | --- |
| Polypropylene resin (aforecited) | 63.75 parts |
| Mineral oil (aforecited) | 35.00 parts |
| Yellow pigment (aforecited) | 1.25 parts |
| Composition of Melt Mixture B | |
| Polypropylene resin (aforecited) | 62.5 parts |
| Mineral oil (aforecited) | 35.0 parts |
| Yellow pigment (aforecited) | 2.5 parts |

There was obtained a porous stretched plastic film wherein a yellow film B is sandwiched between pale yellow films A. The feature of this porous film is as follows.

| Thickness of film (whole thickness) | 105 μm |
| --- | --- |
| Thickness of film A | 35 μm |
| Thickness of film B | 35 μm |
| Porosity | 37% |

Further, the L* values (before oil absorption) of the films A and B were 95.27 and 94.47, respectively, and thus the difference in the L* value between these films was 0.8.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 14

The procedure described in Example 1 was repeated, except that the film A and film B were respectively prepared from the following melt mixtures in this example.

| Composition of Melt Mixture A: | |
| --- | --- |
| Polypropylene resin (aforecited) | 65.0 parts |
| Mineral oil (aforecited) | 35.0 parts |
| Composition of Melt Mixture B: | |
| Polypropylene resin (aforecited) | 62.5 parts |
| Mineral oil (aforecited) | 35.0 parts |
| Yellow pigment (aforecited) | 2.5 parts |

There was obtained a porous stretched plastic film wherein a yellow film B is sandwiched between white films A. The feature of this porous film is as follows.

| Thickness of film (whole thickness) | 105 μm |
| --- | --- |
| Thickness of film A | 35 μm |
| Thickness of film B | 35 μm |
| Porosity | 33% |

Further, the L* values (before oil absorption) of the films A and B were 98.33 and 94.47, respectively, and thus the difference in the L* value between these films was 3.86.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Example 15

The procedure described in Example 1 was repeated, except that the film A and film B were respectively prepared from the following melt mixtures in this example.

| Composition of Melt Mixture A | |
| --- | --- |
| Polypropylene resin (aforecited) | 65.00 parts |
| Mineral oil (aforecited) | 35.00 parts |
| Yellow pigment (aforecited) | 1.25 parts |
| Composition of Melt Mixture B | |
| Polypropylene resin (aforecited) | 64.3 parts |
| Mineral oil (aforecited) | 35.0 parts |
| Red pigment (aforecited) | 0.7 parts |

There was obtained a porous stretched plastic film wherein a red film B is sandwiched between pale yellow films A. The feature of this porous film is as follows.

| Thickness of film (whole thickness) | 105 μm |
| --- | --- |
| Thickness of film A | 35 μm |
| Thickness of film B | 35 μm |
| Porosity | 36% |

Further, the L* values (before oil absorption) of the films A and B were 95.27 and 61.29, respectively, and thus the difference in the L* value between these films was 33.98.

It has been found that this test film exhibits good feeling to the skin and excellent effect of removing oil and can judge the wiping state of oil easily and clearly by a remarkable change in color when used as a cosmetic oil clearing sheet. This film was not broken during the evaluation test.

Subsequently, a change in brightness before and after oil absorption of this porous film was measured according to the same procedure as in Example 1. As a result, the measurement results as described in Table 1 below were obtained.

Comparative Examples

Comparative Examples 1–9

The procedure described in Example 1 was repeated, except that each oil clearing sheet having a single-layer structure was produced for comparison in place of the oil clearing sheet having a three-layer structure according to the following procedure in these example. Production of oil clearing sheet:

A melt mixture prepared as a raw material was cast on a cooling roll through an extrusion die and the resulting film was biaxially stretched (1.8 times in a longitudinal direction, 1.8 times in a width direction). As a result, a porous stretched plastic film was obtained.

The composition of the melt mixture used as the raw material in each Comparative Example and the feature of the resulting porous film (single-layer oil clearing sheet) are described below.

| | COMPARATIVE EXAMPLES 1–9 | | | | | | | | |
|---|---|---|---|---|---|---|---|---|---|
| | Ex. 1 | Ex. 2 | Ex. 3 | Ex. 4 | Ex. 5 | Ex. 6 | Ex. 7 | Ex. 8 | Ex. 9 |
| COMPOSITION OF MELT MIXTURE | | | | | | | | | |
| Polypropylene Resin | 65.0 parts | 63.6 parts | 62.25 parts | 62.75 parts | 58.5 parts | 64.6 parts | 64.3 parts | 63.75 parts | 62.5 parts |
| Mineral Oil | 35.0 parts | 35.0 parts | 35.0 parts | 35.0 parts | 35.0 parts | 35.0 parts | 35.0 parts | 35.0 parts | 35.0 parts |
| Blue Pigment | — | 1.4 parts | 2.75 parts | — | — | — | — | — | — |
| Green Pigment | — | — | — | 3.25 parts | 6.5 parts | — | — | — | — |
| Red Pigment | — | — | — | — | — | 0.4 parts | 0.7 parts | — | — |
| Yellow Pigment | — | — | — | — | — | — | — | 1.25 parts | 2.5 parts |
| FEATURE OF POROUS FILM | | | | | | | | | |
| Color of Film | White | Pale Blue | Blue | Pale Green | Green | Pink | Red | Pale Yellow | Yellow |
| Thickness of Film | 35 μm | 35 μm | 35 μm | 35 μm | 35 μm | 35 μm | 35 μm | 35 μm | 35 μm |
| Porosity | 30% | 30% | 37% | 30% | 33% | 38% | 38% | 35% | 45% |

Subsequently, a change in brightness before and after oil absorption of this porous film was measured according to the same procedure as in Example 1. As a result, the measurement results as described in Table 1 below were obtained.

Comparative Examples 10–17

The procedure described in Example 1 was repeated, except that each oil clearing sheet having a three-layer structure was produced for comparison by changing the melt mixtures A and B used as the raw material as follows.

The composition of the melt mixtures A and B used as the raw material in each Comparative Example and the feature of the resulting porous film (oil clearing sheet having a three-layer structure) are described below.

Comparative Example 10

| Composition of Melt Mixture A | |
|---|---|
| Polypropylene resin (aforecited) | 63.6 parts |
| Mineral oil (aforecited) | 35.0 parts |
| Blue pigment (aforecited) | 1.4 parts |
| Composition of Melt Mixture B | |
| Polypropylene resin (aforecited) | 65.0 parts |
| Mineral oil (aforecited) | 35.0 parts |

Feature of Porous Film

Porous stretched plastic film wherein a white film B is sandwiched between pale blue films A

| Thickness of film (whole thickness) | 105 μm |
|---|---|
| Thickness of film A | 35 μm |
| Thickness of film B | 35 μm |
| Porosity | 30% |

Comparative Example 11

| Composition of Melt Mixture A | |
|---|---|
| Polypropylene resin (aforecited) | 62.25 parts |
| Mineral oil (aforecited) | 35.00 parts |
| Blue pigment (aforecited) | 2.75 parts |
| Composition of Melt Mixture B | |
| Polypropylene resin (aforecited) | 63.6 parts |
| Mineral oil (aforecited) | 35.0 parts |
| Blue pigment (aforecited) | 1.4 parts |

Feature of Porous Film

Porous stretched plastic film wherein a pale blue film B is sandwiched between blue films A

| Thickness of film (whole thickness) | 105 μm |
|---|---|
| Thickness of film A | 35 μm |
| Thickness of film B | 35 μm |
| Porosity | 32% |

Comparative Example 12

Composition of Melt Mixture A

| | |
|---|---|
| Polypropylene resin (aforecited) | 62.50 parts |
| Mineral oil (aforecited) | 35.00 parts |
| Green pigment (aforecited) | 3.25 parts |

Composition of Melt Mixture B

| | |
|---|---|
| Polypropylene resin (aforecited) | 65.0 parts |
| Mineral oil (aforecited) | 35.0 parts |

Feature of Porous Film

Porous stretched plastic film wherein a white film B is sandwiched between pale green films A

| | |
|---|---|
| Thickness of film (whole thickness) | 105 μm |
| Thickness of film A | 35 μm |
| Thickness of film B | 35 μm |
| Porosity | 30% |

Comparative Example 13

Composition of Melt Mixture A

| | |
|---|---|
| Polypropylene resin (aforecited) | 58.5 parts |
| Mineral oil (aforecited) | 35.0 parts |
| Green pigment (aforecited) | 6.5 parts |

Composition of Melt Mixture B

| | |
|---|---|
| Polypropylene resin (aforecited) | 62.50 parts |
| Mineral oil (aforecited) | 35.00 parts |
| Green pigment (aforecited) | 3.25 parts |

Feature of Porous Film

Porous stretched plastic film wherein a pale green film B is sandwiched between green films A

| | |
|---|---|
| Thickness of film (whole thickness) | 105 μm |
| Thickness of film A | 35 μm |
| Thickness of film B | 35 μm |
| Porosity | 32% |

Comparative Example 14

Composition of Melt Mixture A

| | |
|---|---|
| Polypropylene resin (aforecited) | 64.6 parts |
| Mineral oil (aforecited) | 35.0 parts |
| Red pigment (aforecited) | 0.4 parts |

Composition of Melt Mixture B

| | |
|---|---|
| Polypropylene resin (aforecited) | 65.0 parts |
| Mineral oil (aforecited) | 35.0 parts |

Feature of Porous Film

Porous stretched plastic film wherein a white film B is sandwiched between pink films A

| | |
|---|---|
| Thickness of film (whole thickness) | 105 μm |
| Thickness of film A | 35 μm |
| Thickness of film B | 35 μm |
| Porosity | 35% |

Comparative Example 15

Composition of Melt Mixture A

| | |
|---|---|
| Polypropylene resin (aforecited) | 64.3 parts |
| Mineral oil (aforecited) | 35.0 parts |
| Red pigment (aforecited) | 0.7 parts |

Composition of Melt Mixture B

| | |
|---|---|
| Polypropylene resin (aforecited) | 64.6 parts |
| Mineral oil (aforecited) | 35.0 parts |
| Red pigment (aforecited) | 0.4 parts |

Feature of Porous Film

Porous stretched plastic film wherein a pink film B is sandwiched between red films A

| | |
|---|---|
| Thickness of film (whole thickness) | 105 μm |
| Thickness of film A | 35 μm |
| Thickness of film B | 35 μm |
| Porosity | 38% |

Comparative Example 16

Composition of Melt Mixture A

| | |
|---|---|
| Polypropylene resin (aforecited) | 63.75 parts |
| Mineral oil (aforecited) | 35.00 parts |
| Yellow pigment (aforecited) | 1.25 parts |

Composition of Melt Mixture B

| | |
|---|---|
| Polypropylene resin (aforecited) | 65.0 parts |
| Mineral oil (aforecited) | 35.0 parts |

Feature of Porous Film

Porous stretched plastic film wherein a white film B is sandwiched between pale yellow films A

| | |
|---|---|
| Thickness of film (whole thickness) | 105 μm |
| Thickness of film A | 35 μm |
| Thickness of film B | 35 μm |
| Porosity | 33% |

Comparative Example 17

Composition of Melt Mixture A:

| | |
|---|---|
| Polypropylene resin (aforecited) | 62.5 parts |
| Mineral oil (aforecited) | 35.0 parts |
| Yellow pigment (aforecited) | 2.5 parts |

Composition of Melt Mixture B:

| | |
|---|---|
| Polypropylene resin (aforecited) | 63.75 parts |
| Mineral oil (aforecited) | 35.00 parts |
| Yellow pigment (aforecited) | 1.25 parts |

Feature of Porous Film

Porous stretched plastic film wherein a pale yellow film B is sandwiched between yellow films A

| | |
|---|---|
| Thickness of film (whole thickness) | 105 μm |
| Thickness of film A | 35 μm |
| Thickness of film B | 35 μm |
| Porosity | 38% |

Subsequently, a change in brightness before and after oil absorption of this porous film was measured according to the same procedure as in Example 1. As a result, the measurement results as described in Table 1 below were obtained.

TABLE 1

| Example No. | Layer constitution | $L^*$ before oil absorption | $L^*$ after oil absorption | $\delta L^*$ |
|---|---|---|---|---|
| Example 1 | A/B/A | 90.66 | 71.33 | 19.33 |
| Example 2 | A/B/A | 67.93 | 49.67 | 18.26 |
| Example 3 | A/B/A | 90.59 | 66.60 | 23.99 |
| Example 4 | A/B/A | 85.2 | 67.2 | 18.0 |
| Example 5 | A/B/A | 93.54 | 85.54 | 8.00 |
| Example 6 | A/B/A | 84.61 | 62.14 | 22.47 |
| Example 7 | A/B/A | 90.94 | 71.10 | 19.84 |
| Example 8 | A/B/A | 86.1 | 67.3 | 18.8 |
| Example 9 | A/B/A | 92.52 | 78.01 | 14.51 |
| Example 10 | A/B/A | 79.01 | 58.45 | 20.56 |
| Example 11 | A/B/A | 90.34 | 65.73 | 24.61 |
| Example 12 | A/B/A | 96.76 | 93.46 | 3.30 |
| Example 13 | A/B/A | 94.77 | 89.93 | 4.84 |
| Example 14 | A/B/A | 97.16 | 92.57 | 4.59 |
| Example 15 | A/B/A | 90.98 | 68.59 | 22.39 |
| Comp. Ex. 1 | Single layer | 98.33 | 97.18 | 1.15 |
| Comp. Ex. 2 | Single layer | 68.1 | 50.54 | 17.56 |
| Comp. Ex. 3 | Single layer | 61.04 | 40.44 | 20.60 |
| Comp. Ex. 4 | Single layer | 85.99 | 73.41 | 12.58 |
| Comp. Ex. 5 | Single layer | 68.69 | 51.97 | 16.72 |
| Comp. Ex. 6 | Single layer | 80.24 | 68.43 | 11.81 |
| Comp. Ex. 7 | Single layer | 61.29 | 44.13 | 17.16 |
| Comp. Ex. 8 | Single layer | 95.27 | 92.1 | 3.17 |
| Comp. Ex. 9 | Single layer | 94.47 | 90.35 | 4.12 |
| Comp. Ex. 10 | A/B/A | 68.76 | 64.37 | 4.39 |
| Comp. Ex. 11 | A/B/A | 60.98 | 46.23 | 14.75 |
| Comp. Ex. 12 | A/B/A | 85.75 | 82.77 | 2.98 |
| Comp. Ex. 13 | A/B/A | 68.03 | 57.98 | 10.05 |
| Comp. Ex. 14 | A/B/A | 80.21 | 77.87 | 2.34 |
| Comp. Ex. 15 | A/B/A | 61.11 | 51.71 | 9.46 |
| Comp. Ex. 16 | A/B/A | 96.47 | 93.92 | 2.55 |
| Comp. Ex. 17 | A/B/A | 93.83 | 92.07 | 1.76 |

In the column of the layer constitution of Table 1, "A" and "B" denote a film A and a film B, respectively.

Figure 1:
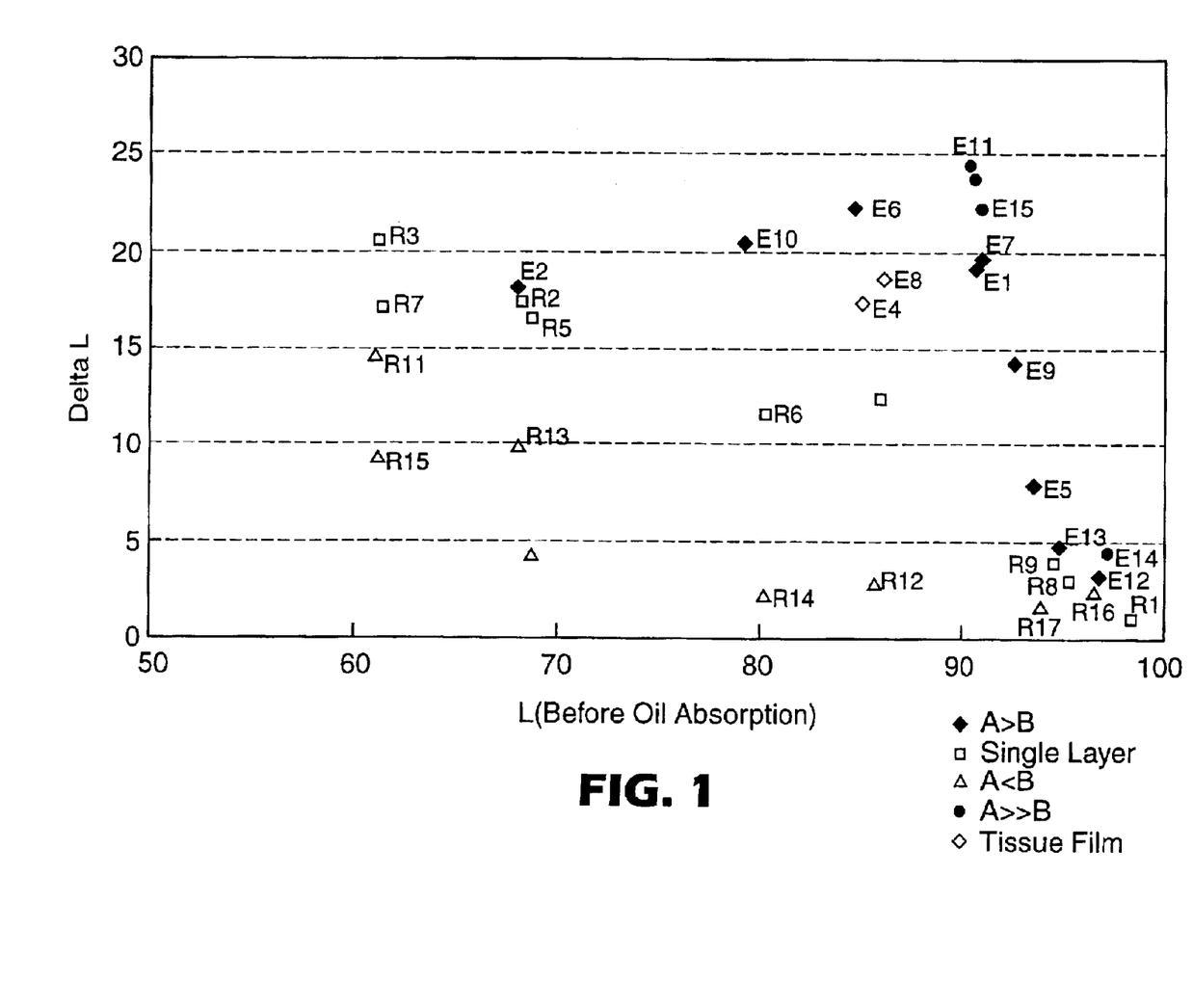
FIG. 1 is a graph plotting a value of L* against δL* before oil absorption in an oil clearing sheet.

FIG. 1 is a graph showing plot of a value of $L^*$ against $\delta L^*$ before oil absorption for the measurement results described in Table 1. In the drawing, E denotes Examples 1 to 15 (Examples of the present invention) and R denotes Comparative Examples 1 to 17. Further, in the left upper column of the graph, "A" denotes a film A, and "B" denotes a film B. Furthermore, symbols □, Δ, ▲, ●, and ◊ denote Comparative Examples (single-layer films), Comparative Examples (those wherein the thickness of the inner layer is smaller than that of the outer layer, examples wherein sufficient effect is not obtained because a value of $L^*$ of the inner layer is high), Examples of the present invention (examples wherein a difference in value of $L^*$ between the outer layer and inner layer is comparatively small), Examples of the present invention (examples wherein a difference in value of $L^*$ between the outer layer and inner layer is comparatively large) and Examples of the present invention (examples using a tissue film wherein the thickness of a single layer is smaller than that of the other examples of the present invention), respectively.

As is apparent from the results described in the graph of FIG. 1 and Table 1, in case where the oil clearing sheet is constituted like the present invention, it is possible to confirm the wiping state of oil easily and clearly, thereby affording sufficiently high satisfactory feeling about wiping of oil. Especially, according to the present invention, it is preferred that a $L^*$ value of the outer layer is larger than that of the inner layer, a difference of the $L^*$ value between these layers is remarkably large, and the film constituting the oil cleaning sheet has a reduced thickness.

As described above, according to the present invention, an oil clearing paper itself is not formed of a paper of a fiber material like a conventional oil clearing paper, but formed of a porous film of a plastic material, thereby enabling fine pores in the film to adsorb oil oozed out on the surface and, at the same time, the porous film is formed of two or more films which differ in brightness. Therefore, not only high capacity to absorb oil can be afforded, but also excellent transparency of the oil-absorbed portion and development of a color of a ground film synergistically acts with each other. As a result, it is possible to confirm the wiping state of sebum easily and clearly, thereby making it possible to afford sufficient wiping feeling and satisfactory feeling to users. Furthermore, this oil clearing sheet has good feeling to the skin and is not broken during the use.

We claim:

1. An oil clearing sheet for makeup comprising a porous stretched film of a plastic material, characterized in that the porous stretched film comprises at least two porous stretched films, which are the same or different, and adjacent films differ in brightness.

2. The oil clearing sheet according to claim 1, wherein the brightness of the porous stretched film is represented by a value of $L^*$ of a CIEL*a*b* color system and a value of $L^*$ of the porous stretched film as an uppermost layer is larger than that of the underlying film under the uppermost layer.

3. The oil clearing sheet according to claim 2, wherein a difference between the value of $L^*$ of the porous stretched film as the uppermost layer and the value of $L^*$ of the underlying film is at least 0.8.

4. The oil clearing sheet according to claim 1, wherein the porous stretched film has the following layer constitution:
   (1) film A/film B,
   (2) film A/film B/film A, or
   (3) film A/film B/film C/film B/film A
wherein a film A is a porous stretched film as an uppermost layer.

5. The oil clearing sheet according to claim 1, wherein the porous stretched film is formed by co-extrusion molding.

6. The oil clearing sheet according to claim 1, wherein the sheet further comprises a hydrophilic liquid absorbing substance.

* * * * *

UNITED STATES PATENT AND TRADEMARK OFFICE
CERTIFICATE OF CORRECTION

PATENT NO.   : 6,943,138 B2
DATED        : September 13, 2005
INVENTOR(S)  : Kono, Yasuhiro

It is certified that error appears in the above-identified patent and that said Letters Patent is hereby corrected as shown below:

Column 5,
Line 61, after "roll" insert -- , --;

Column 9,
Line 63, delete "SZ-EΣ80" and insert -- SZ-Σ80 --.

Signed and Sealed this

Seventeenth Day of January, 2006

JON W. DUDAS
*Director of the United States Patent and Trademark Office*